United States Patent

Hoke, Jr.

[11] Patent Number: 5,994,319
[45] Date of Patent: Nov. 30, 1999

[54] COMBINATION THERAPY FOR ANDROGENIC ALOPECIA WITH ANTISENSE OLIGONUCLEOTIDES AND MINOXIDIL

[75] Inventor: Glenn D. Hoke, Jr., Mount Airy, Md.

[73] Assignee: Dyad Pharmaceutical Corporation

[21] Appl. No.: 08/837,190

[22] Filed: Apr. 14, 1997

Related U.S. Application Data

[60] Provisional application No. 60/015,488, Apr. 15, 1996.

[51] Int. Cl.⁶ ................................................ A61K 48/00
[52] U.S. Cl. ................................... 514/44; 435/6; 514/2; 436/501
[58] Field of Search ................................ 435/6; 436/501; 514/44; 536/22.1, 23.5, 24.5, 24.3–24.33; 935/77, 78

[56] References Cited

U.S. PATENT DOCUMENTS 5,422,262   6/1995   Andersson et al. .................. 435/240.1

OTHER PUBLICATIONS

Drmanac et al. (1990) DNA and Cell Biology, vol. 9, No. 7, pp. 527–534.
Young et al. (1991) Nucleic Acids Res., vol. 19, No. 9, pp. 2463–2470.
Jacobs et al. (1988) Nucleic Acids Res., vol. 16, No. 10, pp. 4637–4650.
Stein et al. (1993) Science, vol. 261, pp. 1004–1012.
New England Biolabs Catalog (1986/87) [Published by New England Biolabs, Beverly, MA, USA], pp. 60–62.
"Finasteride Merck & Co submitted for approval", R&D Focus Drug News, Apr. 7, 1997.
"Merck & Co's Propecia Shows Promise in Hair Loss", Marketletter, Mar. 31, 1997.

*Primary Examiner*—Ardin H. Marschel
*Attorney, Agent, or Firm*—Max Stul Oppenheimer

[57] ABSTRACT

Minoxidil has been shown to stimulate hair growth or inhibit the loss of hair in a number of patients beginning to develop androgenic alopecia. The mechanism by which minoxidil (2,4-pyrimidinediamine, 6-(1-piperidinyl)-3-oxide) alters the hair growth cycle is uncertain, but is thought to act by increasing vascular circulation to the hair follicle. Inhibitors of steroid metabolism, particularly those that inhibit the conversion of testosterone to dihydrotestosterone, have shown effects on hair cycles, including inhibition of hair loss. One class of enzymes targeted by these inhibitors are the steroid 5-alpha reductases. Minoxidil used in conjunction with effectors of steroid metabolism, leads to enhanced hair growth and decreased rates of hair loss. This specification relates to the use of antisense oligonucleotides targeting 5-alpha reductases used in conjunction with other hair growth enhancers and/or hair loss inhibitors.

6 Claims, 4 Drawing Sheets

Elevated DHT levels cause conversion of anagen hair to telogen hair in andorgenic alopecia

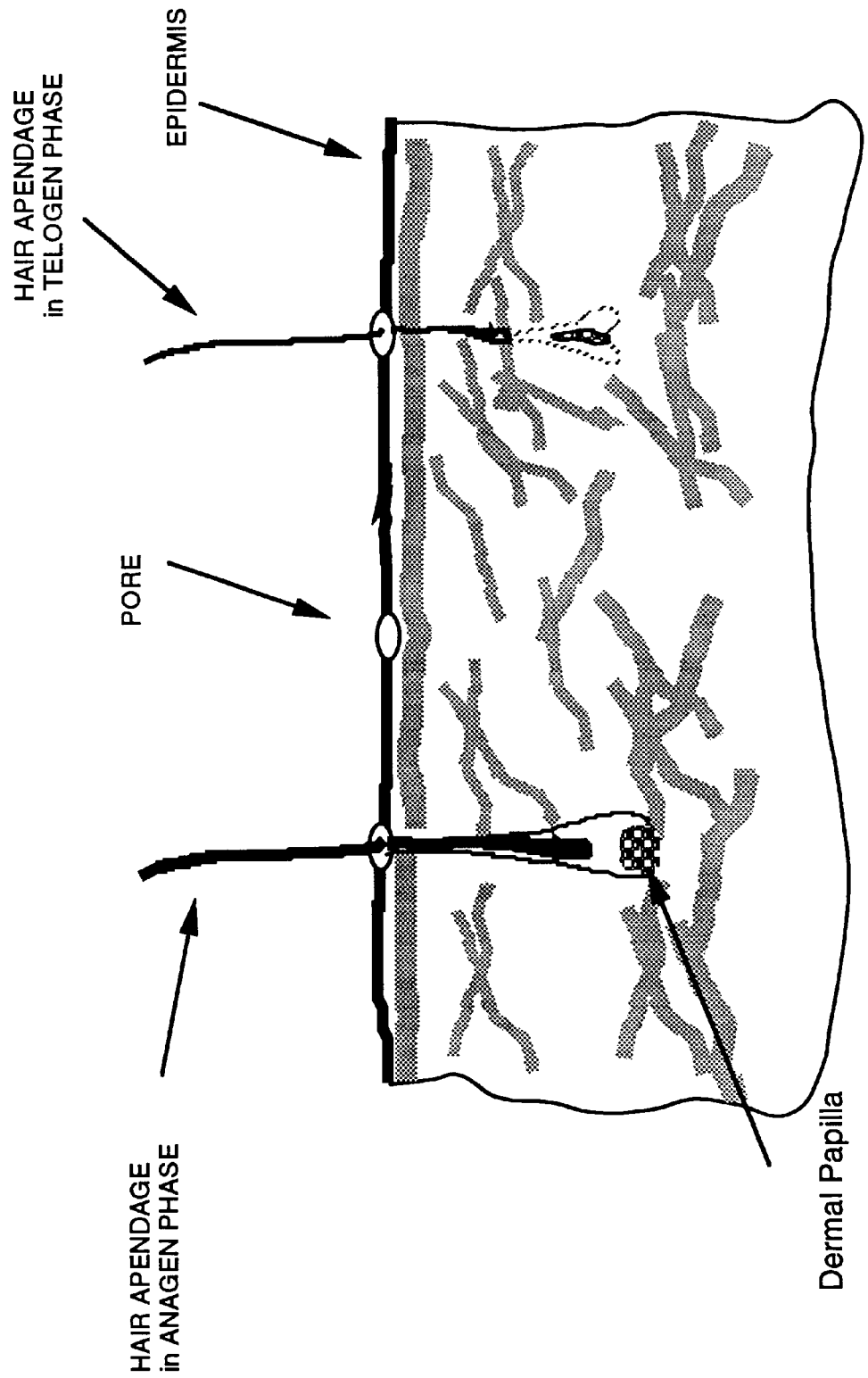
Figure 1 Elevated DHT levels cause conversion of anagen hair to telogen hair in andorgenic alopecia

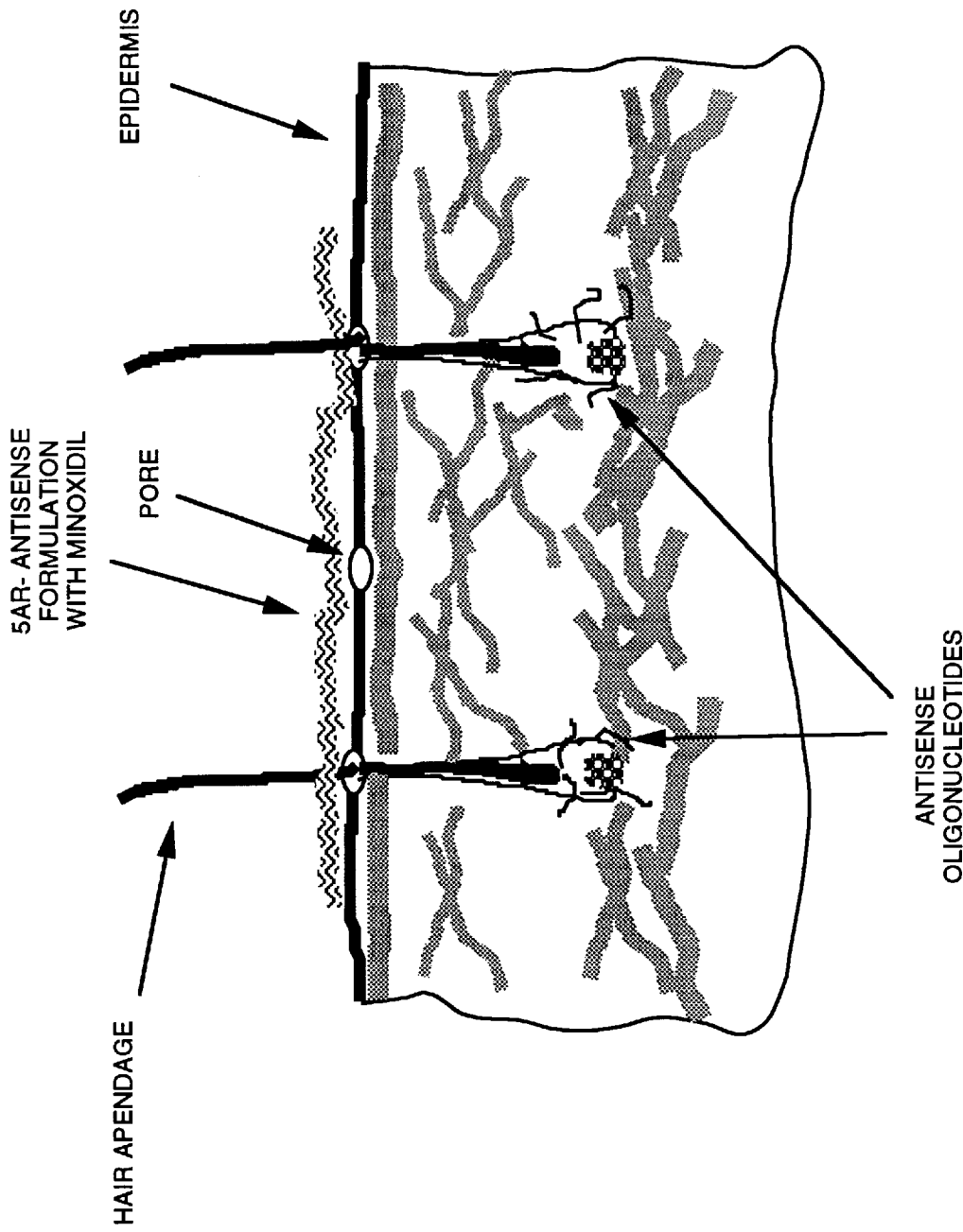
Figure 2. Inhibition of hair loss by antisense targeting 5-alpha reductases and minoxifdil

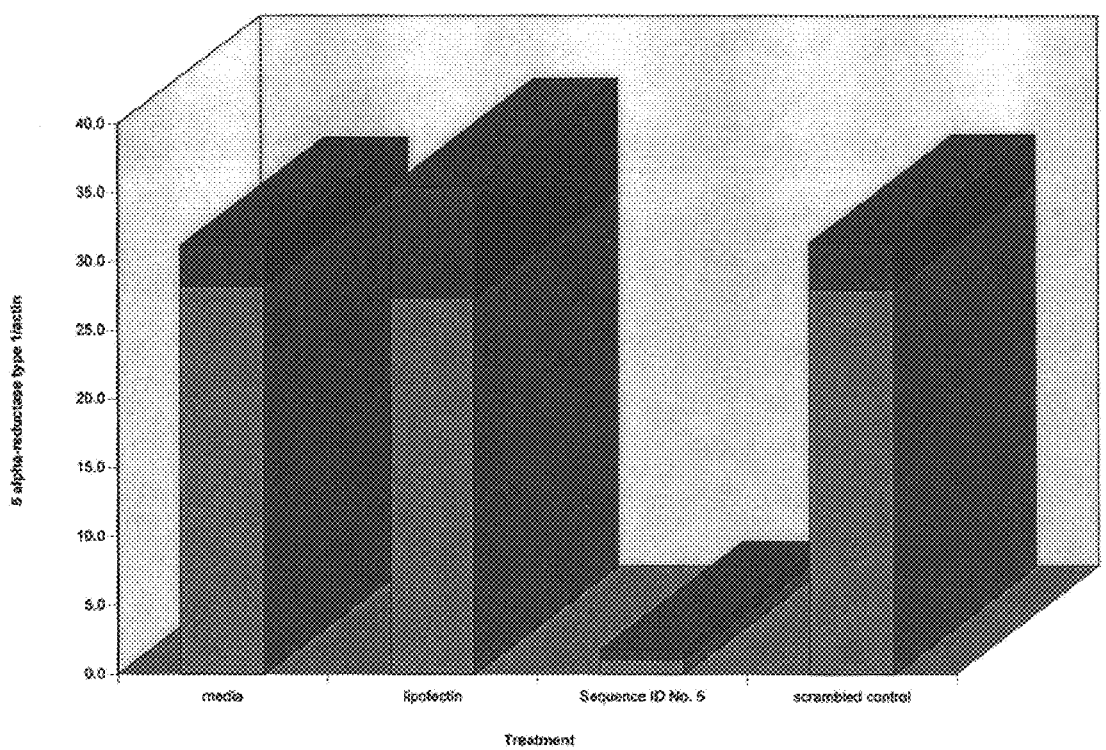

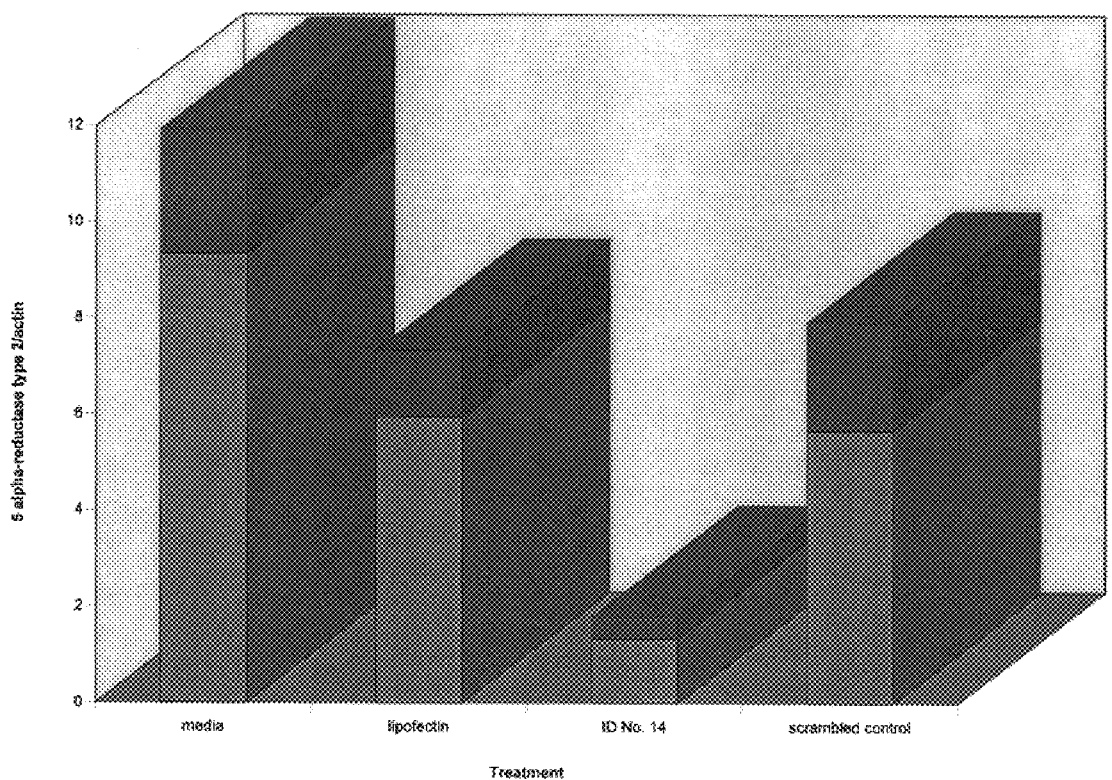

```
                         SEQUENCE LISTING (1) GENERAL INFORMATION:

(iii) NUMBER OF SEQUENCES:  21

(2) INFORMATION FOR SEQ ID NO: 1:

(i) SEQUENCE CHARACTERISTICS:
         (A) LENGTH:  21
         (B) TYPE:   Nucleic Acid
         (C) STRANDEDNESS: Single
         (D) TOPOLOGY:  Linear (iv) ANTI-SENSE:  Yes (xi) SEQUENCE DESCRIPTION: SEQ ID NO: 1:

TGGGCAGCGT GCTCCATGCC C                                                21

(2) INFORMATION FOR SEQ ID NO: 2:

(i) SEQUENCE CHARACTERISTICS:
         (A) LENGTH:  21
         (B) TYPE:   Nucleic Acid
         (C) STRANDEDNESS: Single
         (D) TOPOLOGY:  Linear (iv) ANTI-SENSE:  Yes (xi) SEQUENCE DESCRIPTION: SEQ ID NO: 2:

CAGGGCTGGG CAGCGTGCTC C                                                21

(2) INFORMATION FOR SEQ ID NO: 3:

(i) SEQUENCE CHARACTERISTICS:
         (A) LENGTH:  21
         (B) TYPE:   Nucleic Acid
         (C) STRANDEDNESS: Single
         (D) TOPOLOGY:  Linear (iv) ANTI-SENSE:  Yes (xi) SEQUENCE DESCRIPTION: SEQ ID NO: 3:

TGCCATCGCC AGGGCTGGGC A                                                21

(2) INFORMATION FOR SEQ ID NO: 4:

(i) SEQUENCE CHARACTERISTICS:
         (A) LENGTH:  21
         (B) TYPE:   Nucleic Acid
         (C) STRANDEDNESS: Single
         (D) TOPOLOGY:  Linear (iv) ANTI-SENSE:  Yes
```

(xi) SEQUENCE DESCRIPTION: SEQ ID NO: 4:

TCGCCGTTGC CATCGCCAGG G                                                    21

(2) INFORMATION FOR SEQ ID NO: 5:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 5:

CCCCGTCGCC GTTGCCATCG C                                                    21

(2) INFORMATION FOR SEQ ID NO: 6:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

GGCGCTCCTC CGCCACCCCC G                                                    21

(2) INFORMATION FOR SEQ ID NO: 7:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

GACAGACCAG CTGGCCAGGG C                                                    21

(2) INFORMATION FOR SEQ ID NO: 8:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

GCGCCATTGG AAAGCTTCAA G                                                    21

(2) INFORMATION FOR SEQ ID NO: 9:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

GCGTATTTAG GTACTTATTA G                                                    21

(2) INFORMATION FOR SEQ ID NO: 10:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

TCCAGCCCTA TAGGGGAGG G                                21

(2) INFORMATION FOR SEQ ID NO: 11:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

TGGGCAGCGT GCTCCATGCC C                               21

(2) INFORMATION FOR SEQ ID NO: 12:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 12:

GTGTTCCTCG CCGGTGGCCG C                               21

(2) INFORMATION FOR SEQ ID NO: 13:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 13:

GCGCCGTGTT CCTCGCCGGT G                               21

(2) INFORMATION FOR SEQ ID NO: 14:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

CATCGCGCCG TGTTCCTCGC C                               21

(2) INFORMATION FOR SEQ ID NO: 15:

(i) SEQUENCE CHARACTERISTICS:
        (A) LENGTH: 21

```
          (B) TYPE:    Nucleic Acid
          (C) STRANDEDNESS: Single
          (D) TOPOLOGY: Linear (iv) ANTI-SENSE: Yes (xi) SEQUENCE DESCRIPTION: SEQ ID NO: 15:

CTGCATCGCG CCGTGTTCCT C                                           21

(2) INFORMATION FOR SEQ ID NO: 16:

(i) SEQUENCE CHARACTERISTICS:
          (A) LENGTH:  21
          (B) TYPE:    Nucleic Acid
          (C) STRANDEDNESS: Single
          (D) TOPOLOGY: Linear (iv) ANTI-SENSE: Yes (xi) SEQUENCE DESCRIPTION: SEQ ID NO: 16:

GGCACTGAAC CTGCATCGCG C                                           21

(2) INFORMATION FOR SEQ ID NO: 17:

(i) SEQUENCE CHARACTERISTICS:
          (A) LENGTH:  21
          (B) TYPE:    Nucleic Acid
          (C) STRANDEDNESS: Single
          (D) TOPOLOGY: Linear (iv) ANTI-SENSE: Yes (xi) SEQUENCE DESCRIPTION: SEQ ID NO: 17:

AGGATCCCCG CGGGCACCGC G                                           21

(2) INFORMATION FOR SEQ ID NO: 18:

(i) SEQUENCE CHARACTERISTICS:
          (A) LENGTH:  21
          (B) TYPE:    Nucleic Acid
          (C) STRANDEDNESS: Single
          (D) TOPOLOGY: Linear (iv) ANTI-SENSE: Yes (xi) SEQUENCE DESCRIPTION: SEQ ID NO: 18:

TGGGTCTTTG TGGCTTCAGA G                                           21

(2) INFORMATION FOR SEQ ID NO: 19:

(i) SEQUENCE CHARACTERISTICS:
          (A) LENGTH:  21
          (B) TYPE:    Nucleic Acid
          (C) STRANDEDNESS: Single
          (D) TOPOLOGY: Linear (iv) ANTI-SENSE: Yes (xi) SEQUENCE DESCRIPTION: SEQ ID NO: 19:

GCCACATGTA CTTGGATTGC C                                           21

(2) INFORMATION FOR SEQ ID NO: 20:

(i) SEQUENCE CHARACTERISTICS:
          (A) LENGTH:  21
          (B) TYPE:    Nucleic Acid
          (C) STRANDEDNESS: Single
          (D) TOPOLOGY: Linear (iv) ANTI-SENSE: Yes
```

(xi) SEQUENCE DESCRIPTION: SEQ ID NO: 20:

GAGGGAGGCA TTCAGGCTGC C                                                                  21

(2) INFORMATION FOR SEQ ID NO: 21:

(i) SEQUENCE CHARACTERISTICS:
        (A) LENGTH:  21
        (B) TYPE:   Nucleic Acid
        (C) STRANDEDNESS: Single
        (D) TOPOLOGY:  Linear (iv) ANTI-SENSE:  Yes (xi) SEQUENCE DESCRIPTION: SEQ ID NO: 21:

CACCACTCAG AATCCCCAGG C                                                                  21

COMBINATION THERAPY FOR ANDROGENIC ALOPECIA WITH ANTISENSE OLIGONUCLEOTIDES AND MINOXIDIL

This is a continuation-in-part of Provisional Application Ser. No. 60/015,488, filed Apr. 15, 1996.

FIELD AND BACKGROUND OF THE INVENTION

Field of the Invention

This invention relates to methods of reducing hair loss and promoting hair regrowth, and more particularly to methods using antisense oligonucleotides that effectively reduce the expression of 5-alpha reductase types 1 or 2 in conjunction with the use of (2,4-pyrimidinediamine, 6-(1-piperidinyl)-3-oxide) (commonly known as minoxidil) for the treatment of androgenic alopecia.

DEFINITIONS AND REFERENCES

As used herein, unless otherwise indicated, the term "antisense" or "antisense therapeutic" refers to oligonucleotides, modified oligonucleotides or other chemical compositions that bind in a sequence specific manner to a specified gene, its pre-mRNA, or its mRNA.

As used herein, unless otherwise indicated, the term "oligonucleotide" includes both oligomers of ribonucleotides, i.e. oligoribonucleotides, and oligomers of deoxyribonucleotides, i.e., oligodeoxyribonucleotides or oligodeoxynucleotides.

Unless otherwise indicated, the term "oligonucleotide" also includes oligomers that may be large enough to be termed "polynucleotides."

The terms "oligonucleotide", "oligodeoxynucleotide" and "oligodeoxyribonucleotide" include oligomers and polymers of the biologically significant nucleotides, adenine, deoxyadenine, guanine, deoxyguanine, thymidine, uridine, cytosine and deoxycytosine, as well as oligomers and polymers that contain other novel nucleotides and are capable of forming hybrids with the mRNA transcripts that encode the steroid 5a-reductase type 1. These terms also include oligomers and polymers having one or more purine or pyrimidine moieties, sugar moieties, or internucleotide linkage(s) that have been chemically modified. These terms include any oligomers and polymers that are composed of nucleotides or nucleotides containing any modifications listed above which also contain bases or modified bases that are joined to sugar moieties in the alpha and not the beta configuration (known in the art as "alpha anomers") or any oligonucleotide or polynucleotide that contains one or more of these modifications. The oligonucleotides can be linear or circular and include oligomers that are modified at the 5'-end, 3'-end, or anywhere in the middle of the chain. Modifications may also involve the backbone or may occur through the nucleobases with reporter groups. These reporter groups can be lipids, phospholipids, sugarlipids, etherlipids, peptides, ligands to known or unknown receptors or any other hydrophobic moiety that can enhance or regulate the cellular uptake or the targeting of the oligonucleotide to a particular cell type. The reporter groups can also be a cross-linking group that can form covalent linkages between the oligonucleotide and the targeted mRNA with or without biological or chemical activation. The sugar-phosphate backbone can be joined by 3'-5' or 2'-5' linkages. The backbone modifications of the oligonucleotides may include those known in the art including phosphotriesters, methylphosphonates, phosphodiesters or phosphorothioates and also such backbone modifications which are based on peptides or any other non-phosphate linkages that are currently being employed or might be used by those skilled in the art. These terms also include any oligomer or polymer that has nucleosides, whether natural or containing modifications, that are joined together in linkages that are not 3'-5', such as 3'-2' phosphodiester, 5'-2' phosphodiester, or phosphorothioate linkages.

The term "downstream" is used herein to indicate the 5'-3' direction in a nucleotide sequence. Similarly, the term "upstream" indicates the 3'-5' direction.

The term "mRNA" is used herein to indicate either the mature or processed messenger RNA, or the unprocessed nuclear pre-mRNA that encodes the human steroid 5a-reductase types 1 or 2.

Those references which are cited in the text are incorporated herein; copies of each such reference are attached hereto.

BACKGROUND INFORMATION

The majority of facial and body hair growth is stimulated by androgens. However, the growth of scalp hair has been shown to be inhibited by dihydrotestosterone (DHT) in individuals who exhibit a hereditary predisposition to baldness (Ebling, (1987) Dermatol. Clin S: 467–481; Lucky, (1988), Biochem Soc Trans, 4: 597–602; Brodland and Muller, (1991), Cutis, 47:173–6). The phenotypic expression of baldness does not occur in the absence of androgens. Androgenic alopecia or common baldness represents 99 percent of all cases of hair loss (Brodland and Muller, (1991)). The incidence in men in their third to fifth decade is approximately 47 percent and increases with increasing age. In premenopausal women the incidence is relatively low (9 percent). However, by the sixth decade the occurrence of baldness in women has been estimated at 39 percent.

The mechanism through which androgens, in particular DHT, function to regulate the biology of hair is by modulation of the hair growth cycle (Ebling, (1976;), Biochem Soc Trans, 4: 597–602; Bergfeld and Redmond, (1987), Dermatol Clin, 5: 491–500). The effects of DHT on hair growth appear to be related to local rather than systemic levels of the hormone in that the capacity of scalp skin from balding individuals to convert testosterone ("T") to DHT is greater than that observed in the scalp of non-balding individuals (Ebling, (1976;), Biochem Soc Trans, 4: 597–602; Lucky, (1988), Biochem Soc Trans, 4: 597–602; Schweikert and Wilson, (1974), J Clin Endocrinol Metab, 38: 811–9). Additional evidence supporting the notion that balding is related to an over production of DHT in the scalp is provided by studies with the aza-steroid 4-MA (17b-N, N,-diethylcarbamoyl-4-methyl-4-aza-5a-androstan-3-one) in the stumptail macaque. These monkeys undergo an age-related hair loss similar to that observed in man (Rittmaster, et. al., 1987). In this model system, monkeys treated with the compound grew significantly more hair than did the untreated monkeys or those treated with vehicle alone (Rittmaster, et. al., (1987, J Clin Endocrinol Metab, 65: 188–93). Preliminary biochemical evidence suggests that, in humans, the scalp expresses predominately steroid 5a-reductase 1 (Itami, (1991), Journal of Investigative Dermatology, 95: 57–60). Recent reports have suggested that 4-MA is capable of inhibiting both steroid 5a-reductase isozymes (Andersson et al., (1990), Nature 354: 159–61).

Recent reports show that the use of finasteride (a 5-alpha reductase which blocks the conversion of testosterone to dihydrotestosterone) miniaturizes scalp hair follicles, resulting in the reversal of the balding process. (Marketletter Mar. 31, 1997, "Merck & Co's Propecia Shows Promise in Hair Loss").

The Food and Drug Administration has approved the use of a 2% solution of minoxidil as a topical treatment for male pattern baldness. Through a twice daily application, only 8% of patients reported a dense regrowth of scalp hair, while closer to 33% experienced a moderate regrowth. An additional 33% experiencing little or no regrowth or the growth of vellus hair only and the remaining patients experienced no change in their rate of hair regrowth. The mechanism by which minoxidil stimulates hair growth is unknown. Minoxidil is not thought to affect hair growth or loss by acting at the level that androgens exert their effects.

The use of a combination treatment for androgenic alopecia has been suggested for increasing the effectiveness of minoxidil used alone. For example, the combination of minoxidil treatment with finasteride, a 5-alpha reductase inhibitor, demonstrated that, in combination, these two drugs increased the rate of hair regrowth when compared to either drug administered alone (Diani, A. R. et al., 1992, J. Clin. Endocrinol. Metabol. 74: 345–350).

Antisense oligodeoxynucleotides or ribozymes have been successfully employed to decrease mRNA translation (van der Krol, et. al., 1988; Cohen, 1991; Calabretta, 1991; Calabretta, et. al., 1991; Saison-Behmoraras, et. al., 1991). Once the oligonucleotides are taken up by the cells they can elicit an antisense effect by binding to the correct sequences on the target mRNA. The concept behind antisense therapy is based on the assumption that antisense oligonucleotides are taken up by cells and interact with a specific mRNA resulting in the formation of a stable heteroduplex. The interaction of the antisense oligonucleotide with its target mRNA is highly specific and is determined by the sequence of bases complementary to the antisense oligonucleotide as determined by Watson/Crick base pairing.

The development and progression of androgenic alopecia is associated with the local accumulation of DHT. The enzyme steroid 5a-reductase type 1 is expressed in the inner epithelial sheath of the hair follicle (Wolfgang, E. et al., 1994). This enzyme functions to catalyze the conversion of testosterone to dihydrotestosterone. It would appear that the inhibition of steroid 5a-reductase type 1 expression, alone or in combination with other agents that decrease steroid 5a-reductase activity (i.e. Propecia®)) or through the inhibition of the expression of other steroid 5a-reductase genes, would be an effective means for treating androgenic alopecia. It is possible to lower the intracellular concentration of 5a-reductase by reducing the expression of 5a-reductase. Thus, it would be possible to inhibit the conversion rate of testosterone to DHT via 5a-reductase.

Antisense oligonucleotides used for therapeutic purposes were first proposed in 1978 by M. L Stephenson and P. C. Zamecnik (PNAS 75: 280–284). The concept behind antisense therapy relies on the ability of antisense oligonucleotides to be taken up by cells and form a stable heteroduplex with the target mRNA, thereby down regulating the targeted protein's synthesis.

It has been demonstrated in a number of systems by a number of investigators that oligonucleotides containing an antisense sequence targeting a portion of a particular mRNA are capable of hybridizing to the mRNA and inhibiting the translation of the transcript.

The interaction of an antisense oligonucleotide with target mRNA is highly specific, as hybridization is determined by the sequence of bases complementary to the antisense oligonucleotide (Watson/Crick base pairing of the two strands of nucleic acid). This results in multiple points of contact between the antisense oligonucleotide and the mRNA target, which increases the specificity for hybridization to the correct sequence.

Evidence for down regulation of protein synthesis by antisense oligonucleotides has been well documented in vitro (for reviews see van der Krol, A. R., et al. BioTechniques 6: 958–976, 1988; Milligen et. al. J. Med. Chem 36:1923–1937, 1993. In vivo studies using antisense oligonucleotides have demonstrated that injection of radiolabeled antisense oligonucleotides into the blood of mice results in distribution of full-length labeled oligonucleotide to the various tissues. Once in the tissue, oligonucleotides can elicit an antisense effect by binding to the correct mRNA and, thus, be suitable for a therapeutic (Miller, P. S. and Ts'o, P. O. P. Anticancer Drug Design 2: 117–128, 1987).

More specifically, antisense oligonucleotides targeting 5-alpha reductases have demonstrated the capacity to effectively reduce the synthesis of 5-alpha reductase types 1 or 2. These inhibitors are extremely potent, highly selective, and should not exhibit any of the side effects produced by the anti-androgens (i.e., feminization or impotency).

SUMMARY OF THE INVENTION

It is an object of the invention to provide a treatment to reduce hair loss.

It is a further object of the invention to provide a process for restoring hair.

These and other objects are achieved by providing a process for treatment of androgenic alopecia through inhibition of the expression of human steroid 5a-reductase type 1. Specifically, this invention relates to the use of oligonucleotides, or other chemical compositions that interact in a sequence specific manner to either the steroid 5a-reductase type 1 gene, pre-mRNA or mRNA so as to reduce the transcription or translation of the enzyme used in combination with other agents that reduce the rate of hair loss or increase the rate of hair growth. Clinically, such antisense oligonucleotides could be administered alone or in combination with other agents that decrease steroid 5a-reductase activity (i.e. finasteride) or those having other positive effects in the treatment of androgenic alopecia (i.e., minoxidil). The use of such antisense oligonucleotides to control the expression of steroid 5a-reductase type 1, offers the potential of developing highly specific and efficacious therapies for the adjunctive treatment of diseases characterized by the local over production of DHT. Thus, through the use of antisense inhibitors of 5-alpha reductase expression, it would be possible to provide an increased benefit to patients being treated with minoxidil for androgenic alopecia.

In a preferred embodiment of the invention, therapeutically effective amounts of oligonucleotides can be administered to a patient so as to substantially block the tissue-specific transcription of the human steroid 5a-reductase type 1 (or type 2) gene or the translation of the steroid 5a-reductase type 1 (or type 2) mRNA transcript, thereby substantially reducing the levels of dihydrotestosterone (DHT) in the patient who expresses a condition characterized by the local over production of DHT. It has been demonstrated recently that the use of finasteride (a 5-alpha reductase which blocks the conversion of testosterone to dihydrotestosterone) miniaturizes scalp hair follicles, resulting in the reversal of the balding process. (Marketletter Mar. 31, 1997, "Merck & Co's Propecia Shows Promise in Hair Loss"). By reducing the production of 5-alpha reductase with the antisense oligonucleotides of the present invention, there would be a reduction in the amount of DHT, thereby also leading to a reversal of the balding process. Propecia is administered systemically and unwanted side effects have been reported (Boston Globe, Mar. 25, 1997 "Side effect shadows a new baldness drug"); the present invention may be administered topically, thereby reducing the potential for side effects.

In a preferred embodiment, the pharmaceutical composition is prepared in a form suitable for administration directly or indirectly to areas of the scalp or head that are normally treated for prevention of hair loss resulting from androgenic alopecia. This formulation may include (but is not limited to), wetting agents, liposomes, lipids, oils, emollients, penetration enhancers, or other common additives that are known in the industry and used for topical application.

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

FIG. 1 is a schematic illustration of the mechanism of hair loss due to androgenic alopecia.

FIG. 2 is a schematic illustration of the action of the invention to mitigate hair loss due to androgenic alopecia.

FIG. 3 is graph showing the results of 5 alpha-reductase type 1 inhibition by antisense oligonucleotide Sequence ID No. 5.

FIG. 4 is a graph showing the results of 5 alpha-reductase type 2 inhibition by antisense oligonucleotide Sequence ID No. 14.

DETAILED DESCRIPTION OF THE PREFERRED EMBODIMENT

Referring to FIG. 1, elevated DHT levels cause conversion of anagen hair to telogen hair in androgenic alopecia. Production of DHT by 5-alpha reductases in the dermal papilla initiate the alteration in hair status from anagen to telogen. Elevated DHT levels cause migration of the dermal follicle toward the surface and leads to the dedifferentation of the dermal papilla.

Referring to FIG. 2, topical application of minoxidil and antisense oligonucleotides targeting 5-alpha reductase types I or II result in the therapeutic benefit of minoxidil on hair loss and include benefits from the down regulation of 5-alpha reductase activity. Oligonucleotides delivery to the hair follicle and the dermal papilla is facilitated by the hair appendage. The combination therapy causes a greater protective effect against androgenic alopecia. Minoxidil helps promote hair retention and the antisense oligonucleotides reduce the conversion of testosterone to DHT by 5-alpha reductases in the dermal papilla. Thus, the effects are enhanced and the loss of hair is greatly inhibited compared to minoxidil or antisense oligonucleotides alone.

Antisense oligonucleotides (at a concentration of 0.01 ug to 100 g per kg/body weight) capable of down regulating the expression of either one or both of the human 5-a reductase enzymes is administered to patients experiencing androgenic alopecia in a topical application containing from 0.01–10% minoxidil. Since minoxidil has serious side effects when administered orally, a topical application is preferred. Additionally, recent evidence suggests that it is possible to deliver DNA molecules to the hair follicle by using the hair shaft appendage as an integral component of the delivery strategy (Li. L. et al., 1993). The formulation used for delivery can be comprised of any suitable delivery vehicle that is compatible with the physical properties of antisense oligonucleotides and minoxidil. For example, both of these agents are soluble in a solution of 60% ethanol, propylene glycol, water and, thus, the formulation may be comprised of these components. Additionally, various liposomal formulations may be added to the delivery vehicle to promote delivery to the hair follicle.

The present invention is the result of research regarding the role of androgenic hormones, particularly, dihydrotestosterone (DHT), in the development and progression of androgenic alopecia. Accumulated information has led to the conclusion that a decrease in the concentration of DHT in the scalp will induce a stabilization or improvement of the condition and that such hormonal modulation should constitute a preferred method of treatment.

It has previously been shown that oligonucleotides or modified oligonucleotides, having a nucleotide sequence that is complementary to and that specifically hybridize with at least a portion of a nucleotide sequence that encodes a particular protein are capable of inhibiting the transcription of the gene or the translation of the mRNA transcript, thereby decreasing the concentration of the particular protein.

In accordance with the present invention, an oligonucleotide is provided which has a base sequence capable of hybridizing to the mRNA transcripts of human steroid 5a-reductase types 1 or 2 when administered alone or in combination with other agents that alter the progression of androgenic alopecia (i.e. minoxidil, such as ROGAINE (R) brand produced by Upjohn or finasteride, such as PROPECIA brand produced by Merck). Hybridization of the oligonucleotides to steroid 5a-reductase types 1 or 2 mRNAs substantially blocks the translation of the mRNA transcript. Since the enzyme steroid 5a-reductase is essential for the conversion of testosterone (T) to dihydrotestosterone (DHT), it is anticipated that the level of DHT will decrease in androgen-responsive tissues resulting in therapeutic benefit to patients exhibiting conditions that are characterized by an over production of DHT.

The oligonucleotides of the present invention can be constructed and purified by methods known in the art. The specific oligonucleotide sequences are constructed so as to have a nucleotide sequence that is complementary to a nucleotide sequence that comprises a portion of the gene that encode human steroid 5a-reductase type 1. The described sequences are most often 21 bases in length but may include as few as 3 bases and as many as 100 bases. The targeted sequences have been selected because it is believed that they are essential for the translation of the steroid 5a-reductase type 1 transcript. The oligonucleotides of the present invention have been selected because they are capable of hybridizing with a high degree of specificity to regions of the transcript including the translation initiation site along with sequences 5' or 3' to the translation initiation site. Other oligonucleotides have been selected that hybridize to the 5' cap region of the mRNA or sequences 3' or 5' to the cap site. Additional oligonucleotide sequences of the present invention are complementary to sequences found in the 3' untranslated region of the steroid 5a-reductase genes and are unique to the steroid 5a-reductase genes. Such sequences are capable of hybridizing with specificity to sequences found in the 3'-untranslated region of the steroid 5a-reductase type 1 or 2 mRNA transcripts. In addition to the sequences described above, other sequences contained within the 5a-reductase transcripts are targeted. This strategy has been adopted because, as yet, there is no method currently available that can predict, with precision, sequences that will become effective therapeutics. Moreover, this invention further contemplates antisense oligonucleotides made complementary to any portion of the steroid 5a-reductase genes and which are capable of cross-linking DNA, intercalating DNA or binding more tightly by mechanisms such as, for example, triple stranding. Furthermore, the invention contemplates that any oligonucleotide capable of substantially inhibiting the expression of steroid 5a-reductase type 1 or 2 can be used.

Oligonucleotides of varying lengths have been successfully used to inhibit gene expression. For example, in U.S. Pat. No. 4,806,463 oligonucleotides ranging in size from 12 bases to 26 bases were shown to be incorporated by cells and to be capable of inhibiting the expression of a target mRNA.

In order for the described antisense oligonucleotides to function therapeutically, the oligonucleotides or modified oligonucleotides must be taken up by the cell that expresses the target gene, pre-mRNA, or mRNA. The oligonucleotides of the present invention are constructed so as to insure that the oligonucleotide will pass through the plasma membrane and achieve an intracellular concentration that is sufficient to decrease the expression of steroid 5a-reductases. Oligonucleotides that are constructed to bind to the steroid 5a-reductase type 1 or 2 genes are further modified, if necessary, to enable them to pass through the nuclear membrane in levels that are sufficient to reduce transcription. Recent attempts at enhancing the cellular uptake of antisense oligonucleotides have employed a wide variety of techniques including the use of lipoproteins, (de Schmidt, et. al., 1991), and a wide variety of conjugates, such as poly-L-lysine and cholesterol (Goodchild, 1990). Conjugation of cholesterol to the 5' end of an oligonucleotide has been reported to result in a molecule that exhibited reduced serum clearance due to reduction in renal excretion, compared to that observed with control oligo deoxynucleotides (ODNs) (de Schmidt, et. al., 1991). As a result, the conjugation of cholesterol to ODNs may allow an increase in the delivery of drug to liver cells via the LDL transport mechanism. Liposomes containing antisense oligonucleotides can also be targeted to specific cell types by the addition of cell-specific antibodies (Leonetti, et. al., 1990). These and other methods of achieving and maintaining adequate intracellular concentrations of the oligonucleotides are contemplated by this invention and include other methods and compositions that have the capacity to enhance cellular uptake or decrease the efflux of internalized oligonucleotides. Such modifications should not alter the specificity of the oligonucleotide for its target sequence.

The oligonucleotides of this invention comprise predetermined sequences of DNA ranging in size from about 3 bases up to about 100 bases, which is sufficient to define a unique sequence in one of the human steroid 5a-reductase target transcripts. Less than 10 bases may be used, however the degree of sequence specificity for the mRNA transcripts that encode human steroid 5a-reductases decreases rapidly with decreasing lengths of the oligonucleotides. On the other hand, oligonucleotide sequences greater than about 100 bases may be subject to decreased uptake by cells. It is preferable that the oligonucleotides comprise about 12 to 26 bases. In a most preferred embodiment a 15 to 25-mer oligonucleotide is used.

Antisense oligonucleotides that are intended for use as drugs must achieve sufficient concentrations in order to decrease the expression of a target protein in a manner that provides therapeutic benefit. The oligonucleotides contemplated in this invention are constructed, or otherwise modified, so as to increase their stability by enhancing resistance to various degradative enzymes (e.g., nucleases). Such modifications will function to permit the concentration of the oligonucleotide therapeutic to be maintained at a level that is sufficient so as to realize therapeutic benefit but cannot substantially alter the specificity of the oligonucleotide for its target sequence. Modifications that improve oligonucleotide stability or efficacy include but are not limited to modifications to the phosphate backbone, termini, sugar moieties and the individual nucleic acid bases. Conjugations to peptides, proteins, carbohydrates, lipids, vitamins or any other conjugation that increases therapeutic potency or efficacy can also be used. Also, any modifications resulting in stable secondary structures including circularization of the oligonucleotide and target sequence, and intrastrand joining of the 3' to the 5' termini through covalent bonds or hybridization and triple stranded binding to mRNA can also be made. Any modifications that reduce nuclease sensitivity while substantially maintaining the affinity and substrate specifically and solubility exhibited by unmodified oligonucleotides are within the scope of the invention.

Several chemically modified oligonucleotides have been developed which substantially block or improve resistance to nuclease activity. These oligonucleotide modifications include phosphorothioate oligonucleotides wherein one of the phosphate oxygens is replaced by sulfur. Another type of modification of oligonucleotides is accomplished by replacing the charged phosphate oxygen with a methyl group or other alkyl group. These nonionic DNA analogs include, for example, methyl phosphonates, alkyl-phosphorothioates, and O-alkyl phosphotriesters. A preferred O-alkylphosphotriester is O-methylphosphotriester. Other DNA backbone modifications at the phosphate group include for example, phosphorodithioate, and phosphotriester oligonucleotides or oligonucleotides based on protein-nucleic acid structures or morpholino-like structures.

Various chemical modifications to either or both the 3'- or 5'-termini and the individual nucleic acid bases are known to improve stability of oligonucleotides to nucleases, stabilize the interaction of oligonucleotides with their specific target molecule, or enhance uptake of the oligonucleotides by cells. Moreover, chemical modifications to the 3' or 5' termini or modifications internal to the oligonucleotide can also be introduced as reporter molecules for example, to allow tracking of the oligonucleotide or as lipophilic moieties to enhance cell uptake. Such molecules can be introduced to both unmodified and backbone modified synthetic oligonucleotides. These moieties can be introduced for example, through thio or amino linkages to terminal hydroxyl or phosphate groups or to specific bases.

Other modifications to the oligonucleotides contemplated in this invention include for example, DNA intercalators, photochemically activated cross-linking or cleaving agents, alkylating agents and redox active nucleic acid cleaving groups.

In vivo and in vitro studies of the degradation of chemically modified oligonucleotides have clearly illustrated that modifications to the phosphate backbone, termini, sugar moiety and individual nucleic acids improve oligonucleotide efficacy or stability or both (Goodchild, 1990). Moreover, acute toxicity studies in mice have demonstrated that some modified oligomers are tolerated at about the same concentrations without undesirable side effects as unmodified oligomers.

Regardless of the modifications that are contemplated by this invention, a successful antisense therapeutic that is designed to inhibit the expression of steroid 5a-reductase type 1 must hybridize with sufficient specificity so as to reduce the potential of non-mechanistic-based toxicity. Investigations into the toxicity of other antisense oligonucleotides have not revealed significant damage or lethality to cells. To date In vitro studies examining toxicity of antisense oligonucleotides have been limited primarily to modified oligomers wherein the phosphodiester linkages between the nucleosides have been replaced with either phosphorothioates or methylphosphonates. Under the conditions tested, exposure of a variety of cell lines to phosphorothioate oligomers has not resulted in any significant toxicity.

EXAMPLES

Examples have been included in order to illustrate preferred modes of the invention. Certain aspects of the following examples are described in terms of the techniques and procedures found or contemplated by the present inventor to work well in the practice of the invention. These examples are exemplified through the use of standard laboratory practices on the inventor. In light of the present disclosure and the general level of skill in the art, those of skill will appreciate that the following examples are intended to be exemplary only and that numerous changes, modifications, and alterations can be employed without departing from the spirit and scope of the invention.

Example 1

This example describes the preparation and use of a series of oligonucleotides whose base sequences are substantially complementary to specific nucleotide sequences contained in the human steroid 5a-reductase type 1 or type 2 mRNA transcripts. Oligonucleotides directed against steroid 5a-reductases may be administered alone or in combination with other agents that decrease alter the progression of androgenic alopecia, i.e., minoxidil or Finasteride® or inhibit the expression of other steroid 5a-reductase genes for the treatment of androgenic alopecia. The oligonucleotides are synthesized on an automated DNA synthesizer using standard techniques practiced in the art. In cases where they may be employed, phosphorothioate oligodeoxyribonucleotides are synthesized using standard procedures (Iyer, et. al., 1990). The sequences of oligonucleotides contemplated by this invention and the region of the steroid 5a-reductase type 1 transcript that are being targeted are listed in Tables 1.

Oligonucleotides which may be used as potential inhibitors of human steroid 5a-reductase type 1 biosynthesis include the following:

TABLE 1

Antisense Oligonucleotides Which Target Steroid 5a-Reductase Type 1

| ID No | SEQ. ID NO. | TARGET REGION |
|---|---|---|
| 1524 | 1 | 5'-UNTRANSLATED (21–1) |
| 1525 | 2 | 5'-UNTRANSLATED (27–7) |
| 1526 | 3 | AUG CODON (36–16) |
| 1527 | 4 | AUG CODON (43–23) |
| 1528 | 5 | AUG CODON (48–28) |
| 1529 | 6 | CODING (64–44) |
| 1530 | 7 | CODING (678–658) |
| 1531 | 8 | 3'-UNTRANSLATED (858–838) |

TABLE 1-continued

Antisense Oligonucleotides Which Target Steroid 5a-Reductase Type 1

| ID No | SEQ. ID NO. | TARGET REGION |
|---|---|---|
| 1532 | 9 | 3'-UNTRANSLATED (986–966) |
| 1533 | 10 | 3'-UNTRANSLATED (1240–1220) |

TABLE 2

Antisense Oligonucleotides Which Target steroid 5a-reductase Type 2

| ID No REGION | SEQ. ID NO. | TARGET |
|---|---|---|
| 1674 | 11 | 5'-UNTRANSLATED (1–21) |
| 1675 | 12 | AUG CODON (6–26) |
| 1677 | 13 | AUG CODON (13–33) |
| 1676 | 14 | AUG CODON (10–30) |
| 1678 | 15 | AUG CODON (25–45) |
| 1679 | 16 | CODING (210–230) |
| 1680 | 17 | 3'-UNTRANSLATED (1275–1295) |
| 1681 | 18 | 3'-UNTRANSLATED (1127–1147) |
| 1682 | 19 | 3'-UNTRANSLATED (1860–1880) |
| 1683 | 20 | 3'-UNTRANSLATED (961–981) |

The oligonucleotide sequences contemplated by this invention may be prepared by solid phase synthesis in a DNA synthesizer, by solution phase synthesis or less preferred, through the use of a reverse transcriptase technique. The oligonucleotide can also be prepared, for example, through the use of genetic engineering techniques. Other methods of synthesis are also contemplated by this invention.

While a specific embodiment of the invention has been shown and described in detail to illustrate the application of the principles of the invention, it will be understood that the invention may be embodied otherwise without departing from such principles and that various modifications, alternate constructions, and equivalents will occur to those skilled in the art given the benefit of this disclosure. Thus, the invention is not limited to the specific embodiment described herein, but is defined by the appended claims. In particular, while the invention has been described with respect to a particular category of skin damage resulting from the action of collagenase, it could also be applied to any skin condition resulting from such action.

Example 2

One means of determining the effects of an antisense oligonucleotide on the expression of steroid 5a-reductases is to measure enzyme activity using either cultured cells that normally express the enzyme, such as the human genital skin fibroblast cell line Hs68 (CRL 1635, American Type Culture Collection, Rockville, Md.) or cultured human prostate cells or cell lines that had been transfected with the desired steroid 5a-reductase cDNA. Appropriate cells that are used for this purpose include, but are not limited to, the simian COS cells and human embryonal kidney 293 cells (CRL 1573). Expression plasmids containing the human steroid 5a-reductase type 1 cDNA have been described previously (Andersson and Russell, 1990). Simian COS cells (CRL 1651)were grown and transfected using DEAE dextran. The cells were maintained at 37° C. in an atmosphere of 95% $O_2$, steroid 5% $CO_2$ and propagated according to methods previously described (Jenkins, et. al., 1992; Thigpen and Russell, 1992).

In cells that constitutively express steroid 5a-reductase, oligonucleotides are added to the medium at a concentration of 0.001 to 10.0 mM. In the transient transfection assay, the oligonucleotides are either co-transfected with the steroid 5a-reductase cDNA or added to the medium at a concentration of 0.001 to 10.0 mM following transfection. Cells are plated in multi-well tissue culture plates. The size of the well used for a particular assay is determined by the level of steroid 5a-reductase expressed by a given cell line.

The substrate is prepared by dissolving unlabeled testosterone (Sigma Chemical Co., St. Louis, Mo.) in absolute ethanol followed by the addition of either [7-$^3$H (N)]-testosterone (23.3 Ci/mmole) or [$^{14}$C]-testosterone (50 mCi/mmol) (New England Nuclear, Boston, Mass.). The solvent is evaporated under a stream of nitrogen and the steroids reconstituted in an appropriate medium.

The medium in the sample wells is aspirated and replaced with fresh medium containing the radiolabeled substrate. An additional three wells containing medium and substrate but no cells is also included in order to account for the non-enzymatic metabolism of the substrate. The plates are returned to the incubator and incubated for an appropriate incubation period that is again dependent on the level of steroid 5a-reductase expressed by the cell line.

At the end of the incubation period the medium is collected and transferred to an extraction tube containing 5 ml of toluene-ethanol (9:1), to which has been added 40–250 mg each of unlabeled carrier steroids (estriol, estradiol, estrone, 5a-androstan-3a,17b-diol, 5a-androstan-3b,17b-diol, 4-androstene-3,17-dione, 5a-androstan-3,17-dione, testosterone, and 5a-dihydrotestosterone (Steraloids, Inc. Wilton, N.H.). Depending upon the method used to detect the radiolabeled steroids the extraction solvent may or may not contain 1,000 and 10,000 dpm of [4-$^{14}$C]-dihydrotestosterone (steroid 50–60 mCi/mmol) and [4-$^{14}$C]-testosterone (50 mCi/mmol) (New England Nuclear, Boston, Mass.); respectively. In assays that employ [7-$^3$H (N)]-testosterone as a substrate, the [$^{14}$C]-steroids are included as recovery standards to quantify procedural losses. A small amount of NaCl is also added to the extraction tubes to prevent foaming. The samples are vortexed for approximately 30 seconds and then centrifuged for 10 minutes at 500× g. The organic phase is collected and the solvent evaporated. The steroids are then reconstituted in dichloromethane-methanol (9:1) and analyzed by thin layer chromatography The extracted samples are applied to silica gel 60F$_{254}$, 0.25 mm thick, thin layer chromatography plates (EM Science, Cincinnati, Ohio). The plates are developed in a solvent system consisting of chloroform-ethyl acetate (3:1, Mallinckrodt Inc. Paris, Ky.). The plates are allowed to developed until the solvent front migrates to within 2.0 cm of the top of the plate. After removal from the tanks the plates are air dried. The plates are then viewed under 254 nm UV light and the visible spots marked. The plates are then sprayed with primulin (0.001% in acetone-water (4:1) according to the method of Wright (Moore and Wilson, 1975) which allows the identification of additional steroids under 365 nm UV light. The spots are scraped from the plate using a glass wool plugged Pasteur pipette attached to a vacuum line. The steroids are eluted directly into scintillation vials by the addition of 0.2 ml of dichloromethane followed by two washes of 2.0 ml of methanol. The organic solvent is evaporated, and 10.0 ml of scintillation fluid (Ready Organic, Beckman Instruments, Inc. Fullerton Calif.) are added. Samples are analyzed by liquid scintillation spectrometry. In assays that employ [$^{14}$C]-testosterone as the substrate, steroid metabolism is analyzed directly using the PhosphorImager imaging system (Molecular Dynamics, Inc., San Jose, Calif.).

Following removal of the media for extraction, the cells are washed with phosphate buffered saline (PBS, pH 7.4), and then harvested by exposure to a trypsin-EDTA solution (0.025% trypsin, 0.265 mM EDTA). The cells are collected and centrifuged at 1400× g for 5 minutes. The supernatant is decanted and the cells resuspended in PBS. An aliquot of the cell suspension is counted in a Coulter Counter Model ZM (Coulter Electronics, Ltd., Luton Beds, England). The remaining cells are sonicated and the protein determined according to the method of Bradford (Bradford, 1976). Corrections are made for procedural losses, and the data expressed as percent inhibition based on steroid concentration in terms of picomoles per mg protein or picomoles/$10^5$ cells.

Example 3

It is possible to analyze the proteins of treated and control cells using SDS- denaturing polyacrylamide gel electrophoresis followed by the transfer of resolved proteins to a solid support (Western transfer), such as nitrocellulose, or other filter supper. Filter blots are blocked with non-specific proteins and then analyzed using a primary antibody that recognizes either 5-a reductase type 1 or 2. Following the primary antibody, the blots are then reacted with a second antibody that binds to the first antibody and has incorporated with in the second antibody a reporter moiety (i.e., radioactivity, enzyme linked, or other easily detectable reporter group). Following treatment with the second antibody, the blot is analyzed for the amount of 5-a reductase present in a given amount of cellular protein. Thus, it is possible to actually quantitate the amount of 5-a reductase being expressed in cells.

Chinese hamster ovary cells transfected with the human 5aR-I gene (CHO 1827) or the human 5-aR-II gene (CHO 1829) are plated at 8×106 cells per well, in 6 well dishes in DMEM/FI2(1:1) and 5% Fetal Bovine Serum (FBS). Cells are dosed with ODN's (containing 5 ug/ml LipofectinTM, Life Technologies, Inc. Gaithersburg, Md.) in serum-free Opti-MEM for 3 hr at 37° C. and then returned to serum-containing media. Dosing is carried out for three consecutive days due to the long half-life of the 5aR proteins. Cells are harvested by detachment in PBS with 5 mM EDTA, pelleted, and lysed in a NP40-RIPA buffer. Cellular proteins (5 ug) are then separated by SDS-PAGE on a 12% acrylamide gel before transferring onto a PVDF membrane. The amount of the 5-aR-I or the 5aR-II proteins and actin are then detected by direct visualization using ECL-Western (Amersham, Arlington Heights, Ill.) and antibodies specific for the proteins. Actin is included as an internal control and all results are presented as the ratio of 5aR signal relative to the actin signal. Quantitation is performed using a scanning densitometer and values are compared to controls. FIG. 3 shows the inhibition of 5-aR type I using antisense oligonucleotide Seq. ID No. 5 relative to controls that are untreated, those receiving lipofectin, or a scrambled control oligonucleotide. FIG. 4 shows the inhibition of 5-aR type II using antisense oligonucleotide Seq. ID No. 14 relative to controls that are untreated, those receiving lipofectin, or a scrambled control oligonucleotide.

While a specific embodiment of the invention has been shown and described in detail to illustrate the application of the principles of the invention, it will be understood that the invention may be embodied otherwise without departing from such principles and that various modifications, alternate constructions, and equivalents will occur to those skilled in the art given the benefit of this disclosure. Thus, the invention is not limited to the specific embodiment described herein, but is defined by the appended claims. In particular, while the invention has been described with respect to a particular category of skin damage resulting from the action of collagenase, it could also be applied to any skin condition resulting from such action.

Example 4

A patient suffering from androgenic alopecia caused by the overprotection of steroid 5-alpha reductase, leading to overprotection of DHT, could be treated with at least one oligonucleotide targeting steroid 5-alpha reductases, for example one of the sequences listed in Tables 1 or 2, preferentially one having the sequence CCCCGTCGCC GTTGCCATCG C (Seq. ID No. 5) or CATCGCGCCG TGTTCCTCGC C (Seq. ID No. 14) wherein the intersugar linkages can be comprised of linkages in the 3',5', the 2',5', or mixtures of the two linkages. The oligonucleotides are expected to be incorporated into a suitable pharmaceutically acceptable carrier and administered topically at a concentration of from 0.01 ug to 100 g per kg of body weight. Treatment may be repeated as necessary and the dosage adjusted such that the condition is slowed, halted, or reversed. Additionally, these oligonucleotides may be administered with other agents that are known to slow, halt, or reverse the condition.

What is claimed is:

1. An oligonucleotide having a nucleotide sequence complementary to at least a portion of the pre-mRNA or mature mRNA transcript of human 5-alpha reductase type I or II, said oligonucleotide being hybridizable to said mRNA transcript, wherein the nucleotide sequence (listed in the 5'-3' direction) is:

CATCGCGCCG TGTTCCTCGC C      (SEQ ID NO: 14).

2. An oligonucleotide having a nucleotide sequence consisting of the following sequence (listed in the 5'-3' direction):

CATCGCGCCG TGTTCCTCGC C      (SEQ ID NO: 14).

3. An oligonucleotide having a nucleotide sequence consisting of the following sequence (listed in the 5'-3' direction):

CCCCGTCGCC GTTGCCATCG C      (SEQ ID NO: 5).

4. A composition comprising minoxidil and an oligonucleotide having a nucleotide sequence complementary to at least a portion of the pre-mRNA or mature mRNA transcript of human 5-alpha reductase type I or II, said oligonucleotide being hybridizable to said mRNA transcript, said nucleotide sequence being selected from the group consisting of the following sequence (listed in the 5'-3' direction):

| | | |
|---|---|---|
| 1 | TGGGCAGCGT GCTCCATGCC C | (SEQ ID NO: 1) |
| 2 | CAGGGCTGGG CAGCGTGCTC C | (SEQ ID NO: 2) |
| 3 | TGCCATCGCC AGGGCTGGGC A | (SEQ ID NO: 3) |
| 4 | TCGCCGTTGC CATCGCCAGG G | (SEQ ID NO: 4) |
| 5 | CCCCGTCGCC GTTGCCATCG C | (SEQ ID NO: 5) |
| 6 | GGCGCTCCTC CGCCACCCCC G | (SEQ ID NO: 6) |
| 7 | GACAGACCAG CTGGCCAGGG C | (SEQ ID NO: 7) |
| 8 | GCGCCATTGG AAAGCTTCAA G | (SEQ ID NO: 8) |
| 9 | GCGTATTTAG GTACTTATTA G | (SEQ ID NO: 9) |
| 10 | TCCAGCCCTA TAGGGGGAGG G | (SEQ ID NO: 10) |
| 11 | TGGGCAGCGT GCTCCATGCC C | (SEQ ID NO: 11) |
| 12 | GTGTTCCTCG CCGGTGGCCG C | (SEQ ID NO: 12) |
| 13 | GCGCCGTGTT CCTCGCCGGT G | (SEQ ID NO: 13) |
| 14 | CATCGCGCCG TGTTCCTCGC C | (SEQ ID NO: 14) |
| 15 | CTGCATCGCG CCGTGTTCCT C | (SEQ ID NO: 15) |
| 16 | GGCACTGAAC CTGCATCGCG C | (SEQ ID NO: 16) |
| 17 | AGGATCCCCG CGGGCACCGC G | (SEQ ID NO: 17) |
| 18 | TGGGTCTTTG TGGCTTCAGA G | (SEQ ID NO: 18) |
| 19 | GCCACATGTA CTTGGATTGC C | (SEQ ID NO: 19) |
| 20 | GAGGGAGGCA TTCAGGCTGC C | (SEQ ID NO: 20) |
| 21 | CACCACTCAG AATCCCCAGG C | (SEQ ID NO: 21). |

5. A composition as in claim 14 wherein the nucleotide sequence is:

CCCCGTCGCC GTTGCCATCG C      (SEQ ID NO: 5).

6. A composition as in claim 14 wherein the nucleotide sequence is:

CATCGCGCCG TGTTCCTCGC C      (SEQ ID NO: 14).

* * * * *